United States Patent
Nandabalan et al.

(10) Patent No.: US 10,610,563 B2
(45) Date of Patent: Apr. 7, 2020

(54) USE OF UBIQUITIN-PROTEASOME SYSTEM INHIBITORS FOR TREATMENT OF TUMORS ASSOCIATED WITH NEUROFIBROMATOSIS TYPE-2

(71) Applicant: BIOXCEL CORPORATION, Branford, CT (US)

(72) Inventors: Krishnan Nandabalan, Guilford, CT (US); Sameer Sharma, Kangra (IN); Luca Rastelli, Norwell, CT (US)

(73) Assignee: BIOXCEL CORPORATION, Branford, CT (US)

( * ) Notice: Subject to any disclaimer, the term of this patent is extended or adjusted under 35 U.S.C. 154(b) by 0 days.

(21) Appl. No.: 15/529,730

(22) PCT Filed: Nov. 24, 2015

(86) PCT No.: PCT/US2015/062347
§ 371 (c)(1),
(2) Date: May 25, 2017

(87) PCT Pub. No.: WO2016/085943
PCT Pub. Date: Jun. 2, 2016

(65) Prior Publication Data
US 2017/0360872 A1    Dec. 21, 2017

Related U.S. Application Data

(60) Provisional application No. 62/126,749, filed on Mar. 2, 2015, provisional application No. 62/084,276, filed on Nov. 25, 2014.

(51) Int. Cl.
| | | |
|---|---|---|
| *A61K 38/05* | (2006.01) | |
| *A61K 45/06* | (2006.01) | |
| *A61K 38/07* | (2006.01) | |
| *A61K 31/69* | (2006.01) | |
| *A61K 31/573* | (2006.01) | |
| *A61P 35/00* | (2006.01) | |
| *G01N 33/574* | (2006.01) | |

(52) U.S. Cl.
CPC .......... *A61K 38/05* (2013.01); *A61K 31/573* (2013.01); *A61K 31/69* (2013.01); *A61K 38/07* (2013.01); *A61K 45/06* (2013.01); *A61P 35/00* (2018.01); *G01N 33/57407* (2013.01); *G01N 33/57423* (2013.01); *G01N 2333/82* (2013.01); *G01N 2800/52* (2013.01)

(58) Field of Classification Search
CPC ...... A61K 38/05; A61K 31/573; A61K 31/69; A61K 38/07; A61K 45/06; A61P 35/00
USPC ........................................................ 514/64
See application file for complete search history.

(56) References Cited

U.S. PATENT DOCUMENTS

| | | | |
|---|---|---|---|
| 7,514,207 B2 | 4/2009 | Jacks et al. | |
| 2005/0084490 A1 | 4/2005 | Adams et al. | |
| 2012/0157401 A1 | 6/2012 | Cao et al. | |
| 2013/0202659 A1* | 8/2013 | Crawford ............... | A61K 47/60 424/400 |
| 2014/0011699 A1 | 1/2014 | Testa et al. | |
| 2014/0128434 A1 | 5/2014 | Auger et al. | |

FOREIGN PATENT DOCUMENTS

| | | |
|---|---|---|
| CN | 104958769 A | 10/2015 |
| WO | WO 2007/143629 A1 | 12/2007 |
| WO | WO 2007/143630 A2 | 12/2007 |
| WO | WO 2008/075376 A1 | 6/2008 |
| WO | WO 2013/078059 A1 | 5/2013 |
| WO | WO 2014/097306 A1 | 6/2014 |
| WO | WO 2015/002078 A1 | 1/2015 |
| WO | WO 2016/085943 A1 | 6/2016 |
| WO | WO 2017/020974 A1 | 2/2017 |

OTHER PUBLICATIONS

Angelo et al. Combining Curcumin (diferuloylmethane) and heat shock protein inhibition for neurofibromatosis 2 treatment: analysis of response and resistance pathways, 2011, Molecular Cancer Therapeutics, 10 (11), 2095-2103. (Year: 2011).*
Fennell et al Oncogene, 2008, 27, 1189-1197 (Year: 2008).*
Angelo, Laura, et al., "Combining Curcumin (Diferuloylmethane) and Heat Shock Protein Inhibition for Neurofibromatosis 2 Treatment: Analysis of Response and Resistance Pathways." Molecular Cancer Therapeutics (2011); 10(11): 2094-2103.
Extended European Search Report for European Application No. EP 15863990.6, dated Apr. 3, 2018, 6 pages.
Landis-Piwowar, K.R., et al., "The proteasome as a potential target for novel anticancer drugs and chemosensitizers." Drug Resistance Updates (2006); 9(6): 263-273.
Karajannis and Ferner, "Neurofibromatosis-related tumors: emerging biology and therapies." Curr Opin Pediatr. (2015); 27 (1): 26-33.
Morrow and Shevde, "Merlin: The wizard requires protein stability to function as a tumor suppressor." Biochim Biophys Acta. (2012); 1826 (2): 400-406.
Zhou and Hanemann, "Merlin, a multi-suppressor from cell membrane to the nucleus." FEBS Letter (2012); 586 (10): 1403-1408.
PCT/US2015/062347, International Preliminary Report on Patentability dated May 30, 2017, 9 pages.
PCT/US2015/062347, International Search Report and Written Opinion dated Feb. 3, 2016, 11 pages.
Ammoun et.al, "Nilotinib alone or in combination with selumetinib is a drug candidate for neurofibromatosis type 2." Neuro Oncol. (2011); 13(7): 759-766.

(Continued)

*Primary Examiner* — Yevgeny Valenrod
(74) *Attorney, Agent, or Firm* — Cooley LLP

(57) ABSTRACT

The invention discloses a method of treating, preventing or ameliorating tumor or symptoms resulting from defective neurofibromatosis type-2 gene in a subject by administering to the subject a therapeutically effective amount of a ubiquitin-proteasome system inhibitor which inhibits or slows the growth of neurofibromatosis type-2-deficient tumor or associated symptoms. The invention also includes methods of diagnosis and screening of patients for neurofibromatosis type-2 and mesothelioma.

25 Claims, 9 Drawing Sheets

(56) References Cited

OTHER PUBLICATIONS

Carbone and Yang. "Molecular Pathways: Targeting Mechanisms of Asbestos and Erionite Carcinogenesis in Mesothelioma." Clinical Cancer Research (2012); 18(3): 598-604. [Published Online First Nov. 7, 2011.].
Karajannis, et al., "Phase II study of everolimus in children and adults with neurofibromatosis type 2 and progressive vestibular schwannomas," Neuro Oncol.(2014); 16(2): 292-297.
Li, W., et al. "Merlin/NF2 loss-driven tumorigenesis linked to $CRL4^{DCAF1}$-mediated inhibition of the Hippo pathway kinases Lats1 and 2 in the nucleus." Cancer Cell (2014); 26(1): 48-60.
Sartore-Bianchi, A., et al. "Bortezomib Inhibits Nuclear Factor-kB-Dependent Survival and Has Potent In vivo Activity in Mesothelioma." Clinical Cancer Research (2007); 13(19): 5942-5951.
Utermark, T., et al., "Reduced Apoptosis Rates in Human Schwannomas." Brain Pathology (2005); 15(1): 17-22.
Adams et.al, "PT-100, a Small Molecule Dipeptidyl Peptidase Inhibitor, Has Potent Antitumor Effects and Augments Antibody-Mediated Cytotoxicity via a Novel Immune Mechanism," Cancer Research 64, 5471-5480, Aug. 1, 2004.
Duncan et al., "A pan-inhibitor of DASH family enzymes induces immunemediated regression of murine sarcoma and is a potent adjuvant to dendritic cell vaccination and adoptive T-cell therapy" J Immunother. Oct. 2013 ; 36(8), 21 pages.
Egger et al., "Effects of the fibroblast activation protein inhibitor, PT100, in a murine model of pulmonary fibrosis," European Journal of Pharmacology, vol. 809, Aug. 15, 2017, pp. 64-72.
Feig et al., "Targeting CXCL12 from FAP-expressing carcinoma-associated fibroblasts synergizes with anti-PD-LI immunotherapy in pancreatic cancer," Proc. Natl. Acad. Sci. USA 110(50): 20212-20217 (2013).
Da Silva et al., "Dipeptidylpeptidase 4 inhibition enhances lymphocyte trafficking, improving both naturally occurring tumor immunity and immunotherapy," Nature Immunology vol. 16, No. 8, Aug. 2015.
Wong et al., "Neuropeptide Y is a physiological substrate of fibroblast activationprotein: Enzyme kinetics in blood plasma and expression of Y2R andY5R in human liver cirrhosis and hepatocellular carcinoma," Peptides 75 (2016) 80-95.

* cited by examiner

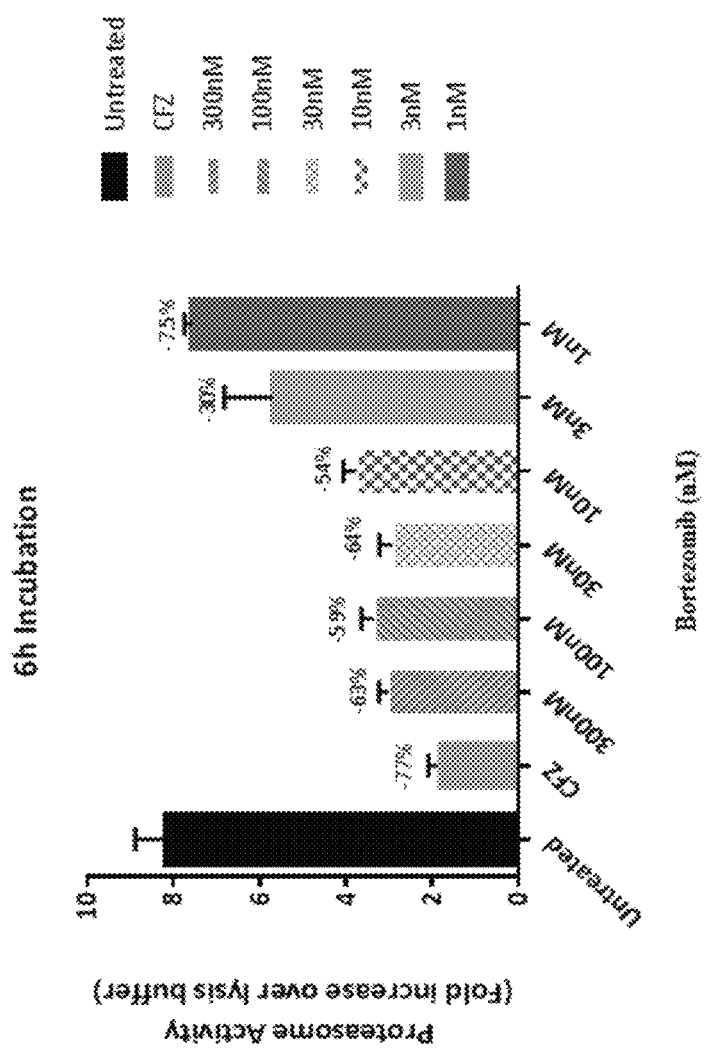
Figure 1: 20S Proteasome Assay of Bortezomib at conc. of 1nM, 3nM, 10nM, 30nM, 100nM and 300nM in the NF2 knockout cell line. Carfilzomib (CFZ) was used as a reference compound for 6hrs incubation time

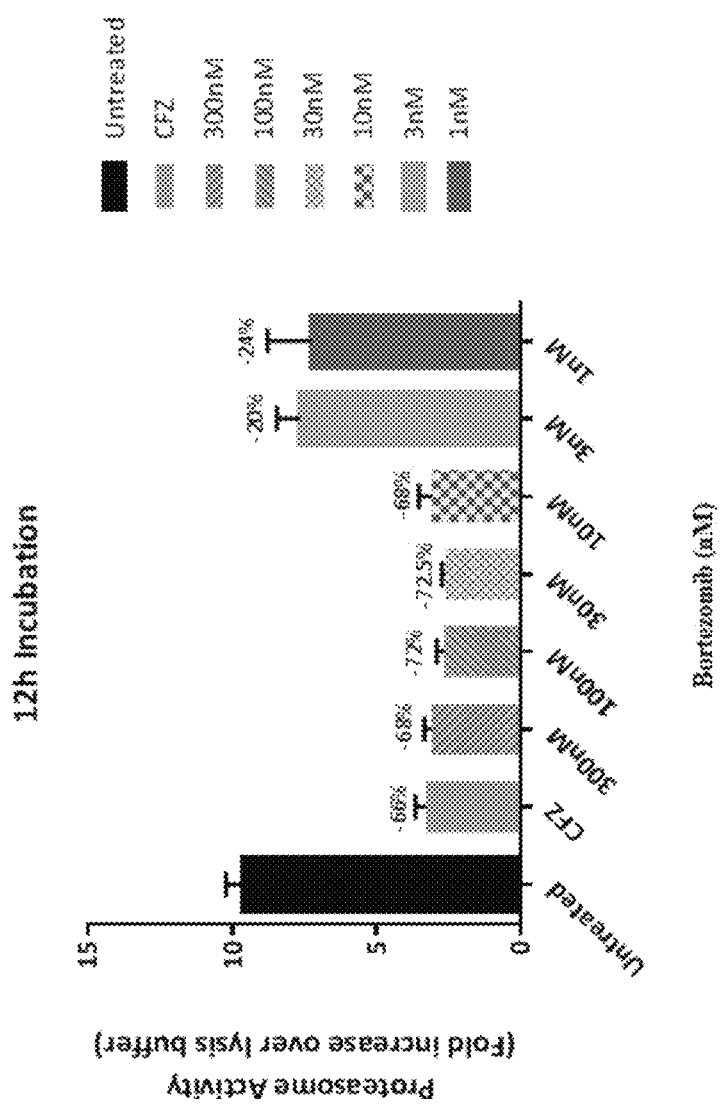
Figure 2: 20S Proteasome Assay of Bortezomib at conc. of 1nM, 3nM, 10nM, 30nM, 100nM and 300nM in the NF2 knockout cell line. Carfilzomib (CFZ) was used as a reference compound for 12hrs incubation time

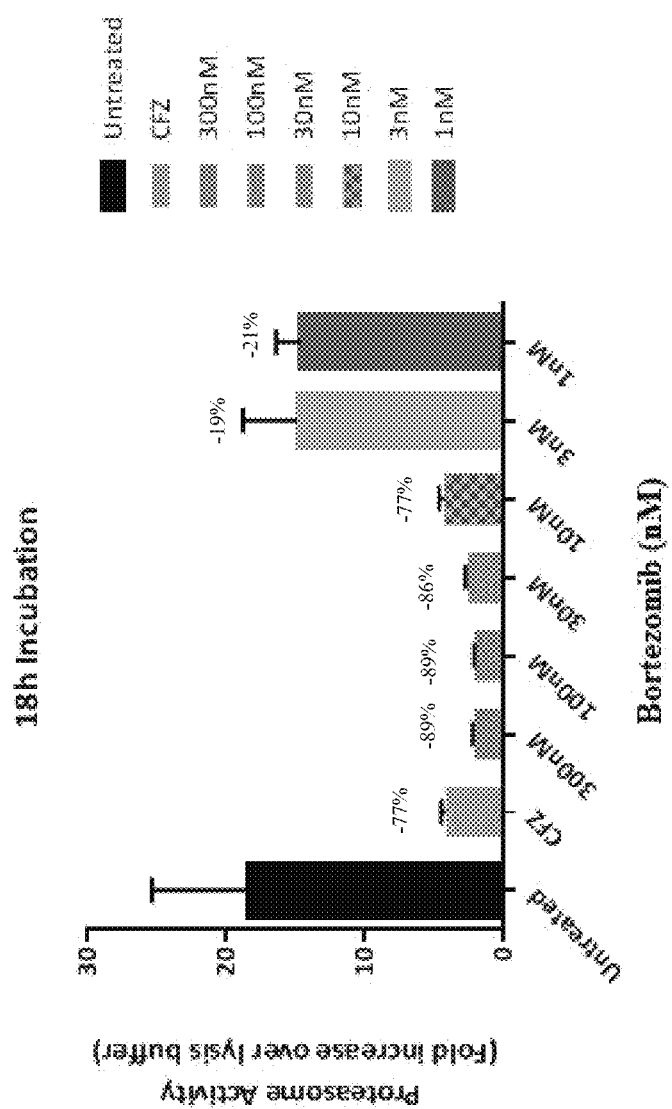
Figure 3: 20S Proteasome Assay of Bortezomib at conc. of 1nM, 3nM, 10nM, 30nM, 100nM and 300nM in the NF2 knockout cell line. Carfilzomib (CFZ) was used as a reference Compound for 18hrs incubation time

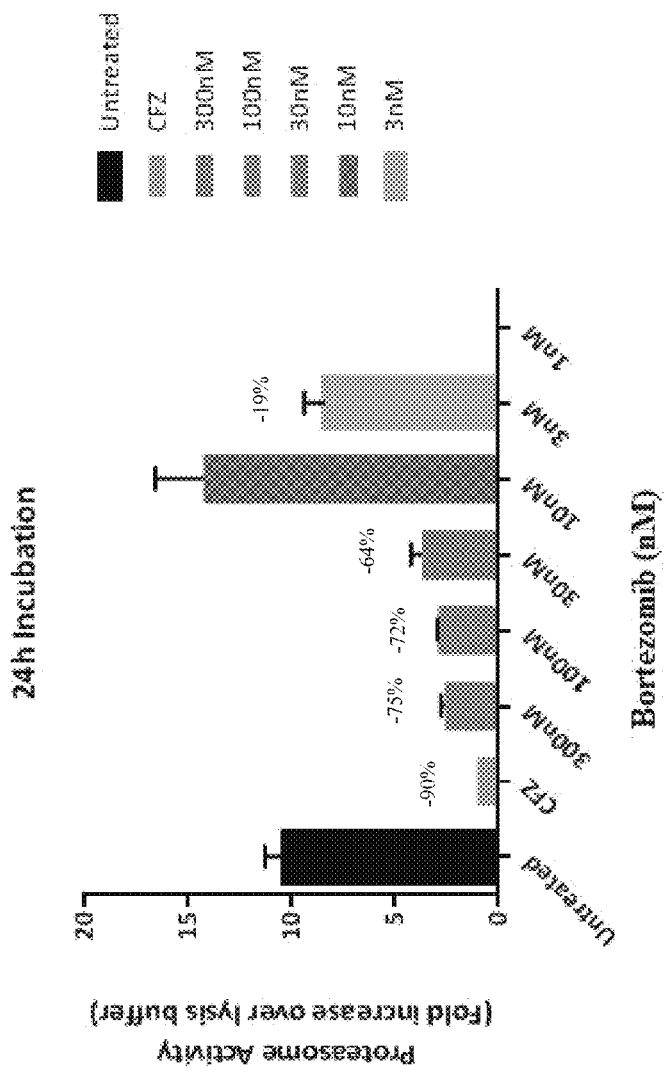
Figure 4: 20S Proteasome Assay of Bortezomib at conc. of 1nM, 3nM, 10nM, 30nM, 100nM and 300nM in the NF2 knockout cell line. Carfilzomib (CFZ) was used as a reference compound for 24hrs incubation time

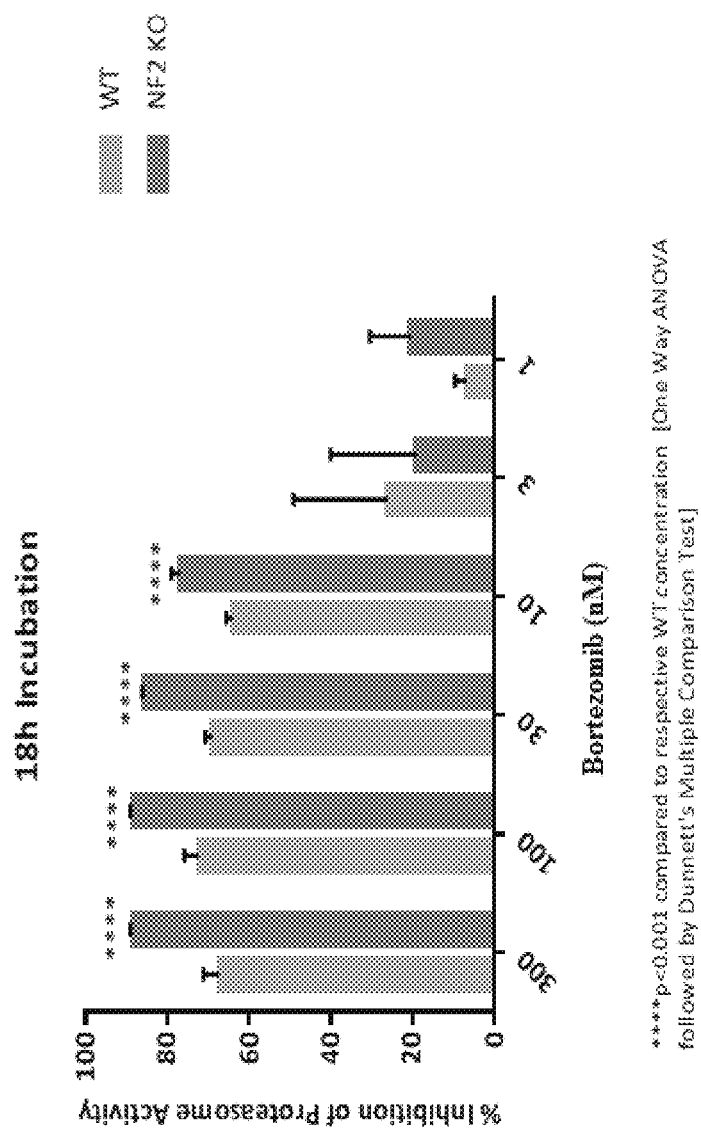
Figure 5: Percentage (%) inhibition of Proteasome activity of bortezomib at conc. of 1nM, 3nM, 10nM, 30nM, 100nM and 300nM in the NF2 knockout/wild type haploid cell line with 18 hrs incubation time interval.

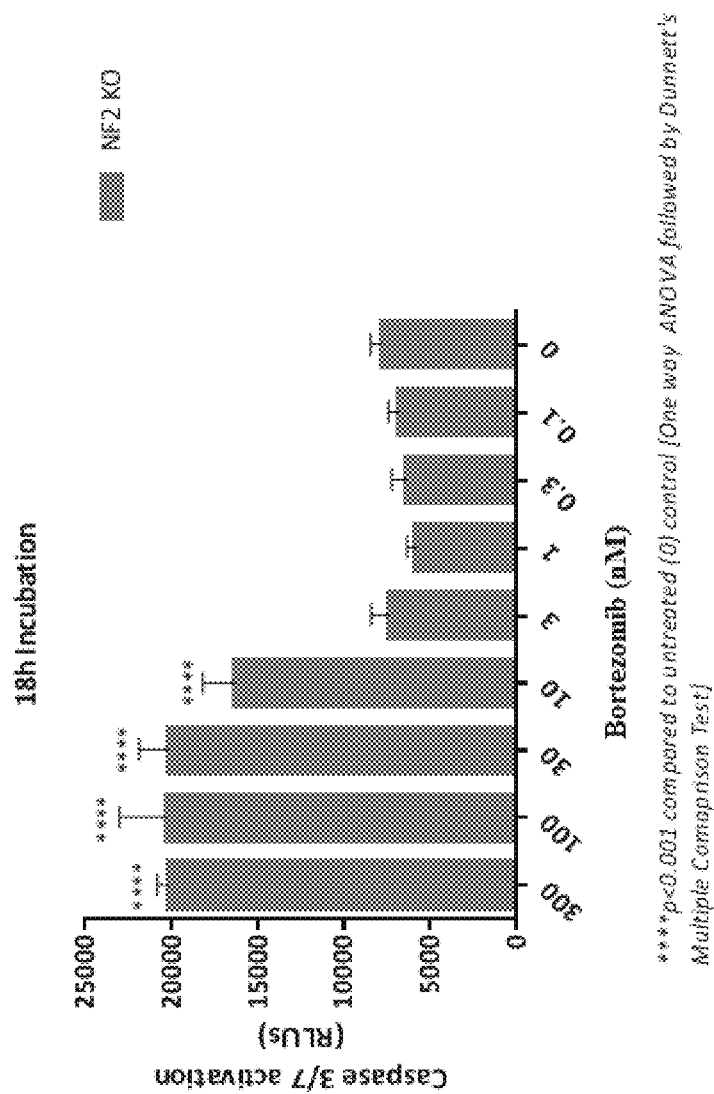
Figure 6: Caspase 3/7 activity for Bortezomib at conc. of 0.1 nM, 1nM, 3nM, 10nM, 30nM, 100nM and 300nM in the NF2 knockout cell line. Staurosporine (1 & 10 μM) was used as a reference compound. Time intervals observed was 18 hrs.

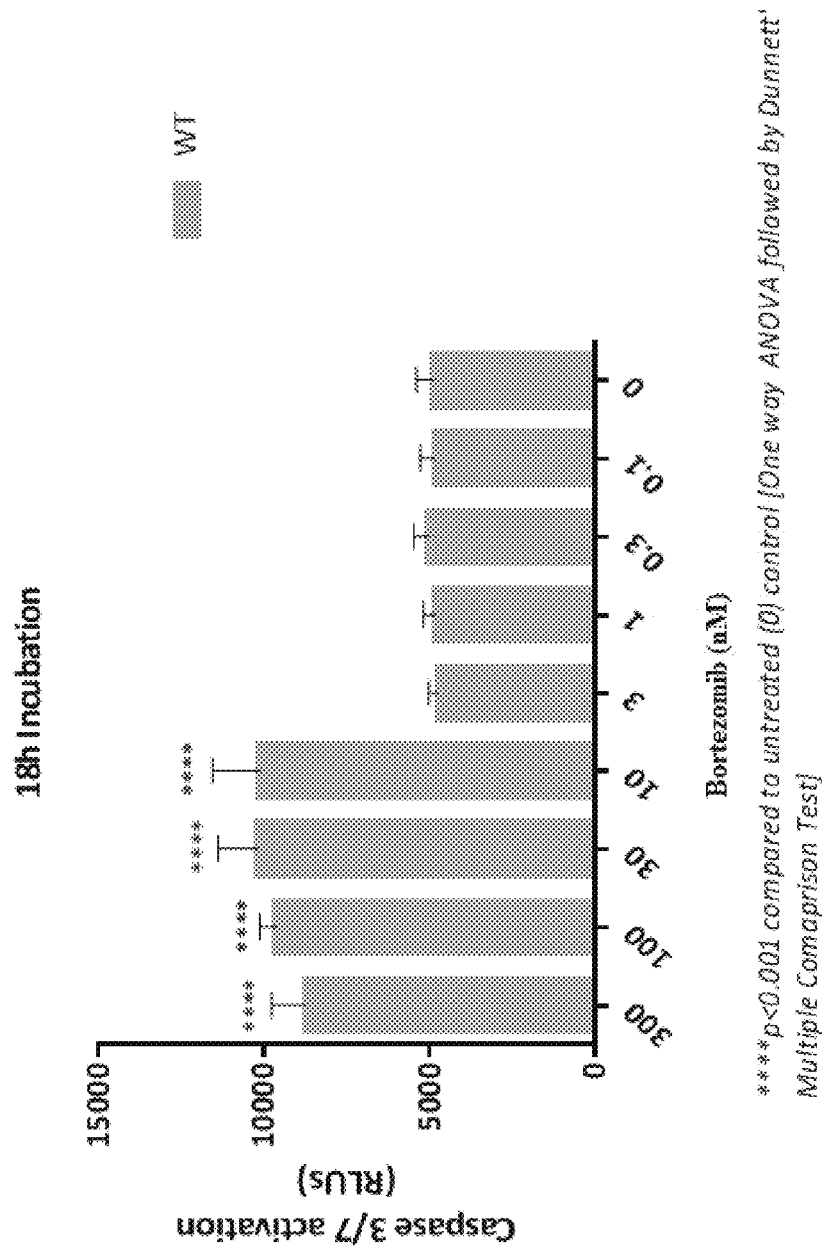
Figure 7: Caspase 3/7 activity for Bortezomib at conc. of 0.1 nM, 1nM, 3nM, 10nM, 30nM, 100nM and 300nM in the wild type haploid cell line. Staurosporine (1 & 10 μM) was used as a reference compound. Time intervals observed was 18 hrs.

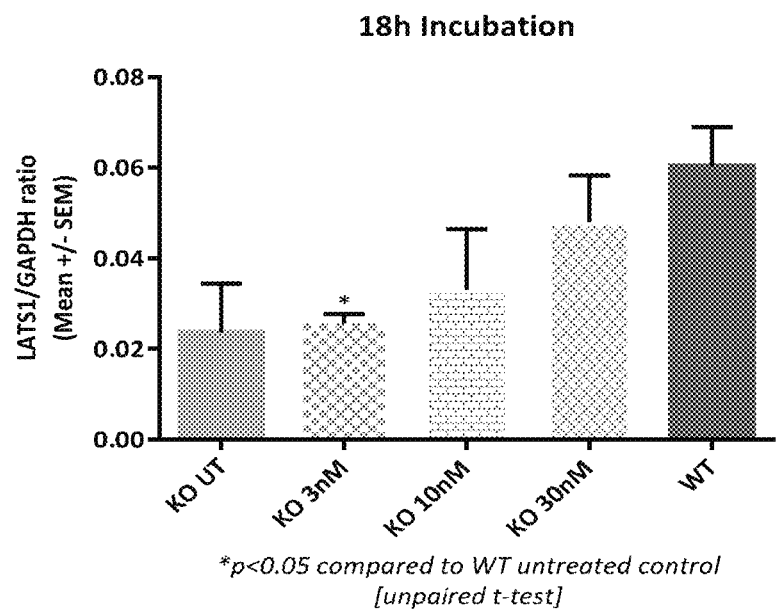
Figure 8: Western Blot analysis for bortezomib tested at concentration of 3 nM, 10 nM and 30nM, in the NF2 knockout cell line (KO). Also shown is the wild type haploid cell line (WT) for LATS1 levels. UT:Untreated.

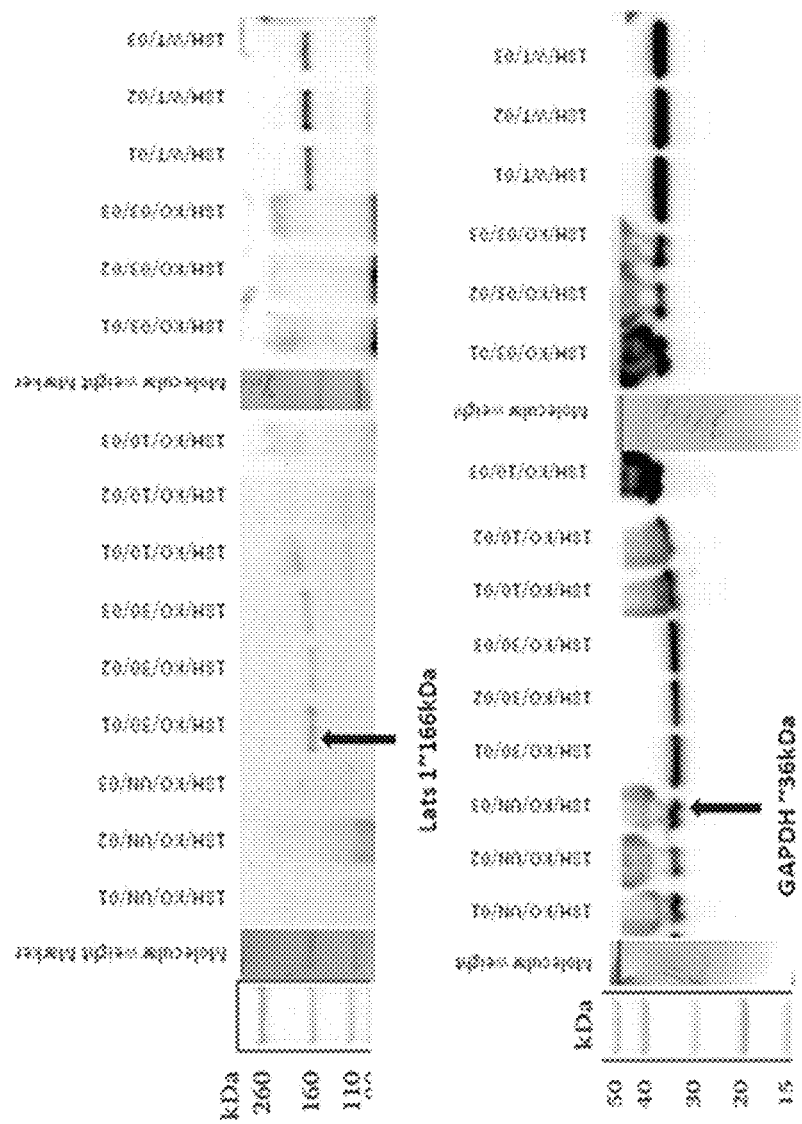
Figure 9: Western Blot analysis blot for bortezomib tested at conc. of 3 nM, 10 nM and 30nM (three lanes for each concentration) in the NF2 knockout (KO) cell line along with untreated (UN) NF2 knockout control and untreated wild type control with 18 hrs incubation. Also shown is the GAPDH (Endogenous Control) as standard control.

USE OF UBIQUITIN-PROTEASOME SYSTEM INHIBITORS FOR TREATMENT OF TUMORS ASSOCIATED WITH NEUROFIBROMATOSIS TYPE-2

CROSS REFERENCE TO RELATED APPLICATIONS

This application is the National Stage of International Application No. PCT/US2015/062347, filed Nov. 24, 2015, which claims the benefit of priority to U.S. Provisional Application Ser. No. 62/084,276, filed Nov. 25, 2014, and 62/126,749, filed Mar. 2, 2015, the contents of each are herein incorporated by reference in their entireties.

FIELD OF INVENTION

The present invention relates to novel therapies and methods of treating cancer. More specifically, the present invention relates to method of treating tumors associated with cells that have mutations in neurofibromatosis type-2 gene using an ubiquitin-proteasome system inhibitor.

BACKGROUND

Neurofibromatosis is a genetic disorder that affects bone, soft tissue, skin and nervous system. It is classified into neurofibromatosis type 1 and neurofibromatosis type-2. Neurofibromatosis type-2 is caused by the mutations in neurofibromatosis type-2 gene on chromosome 22. Neurofibromatosis type-2 deficient tumors are unique in that they are slow growing tumors. The Neurofibromatosis type-2 gene encodes the merlin protein which has tumor suppressor functions.

Several pathways have been targeted for the treatment of tumors associated with neurofibromatosis type-2. U.S. Pat. No. 7,514,207 patent discloses that inhibition of p21 activated kinase (PAK) or merlin phosphorylation helps in the treatment of neurofibromatosis type-2. P21 activated kinase are well-known regulators of cytoskeletal remodelling and cell motility, but have recently also have been shown to promote cell proliferation.

WO2007143629 ("WO'629") also discloses that inhibition of the AKT/Protein Kinase B is useful for the treatment of neurofibromatosis type-2. WO'629 is directed to a method of treating tumors resulting from the neurofibromatosis type-2 using compounds that inhibit the PI3K/AKT signalling or the proteins of the pathway. PAK and AKT/Protein kinase B inhibitors treat neurofibromatosis type-2 by merlin inactivation. So, it is beneficial only when the merlin is involved. However, these pathways may not be effective where other causes are involved.

U.S. published patent application US20140128434 discloses the treatment of neurofibromatosis type-2 by inhibiting tyrosine kinase/focal adhesion kinase (FAK) pathway. Tyrosine kinase inhibitors inhibit the activity of EGFR (Epidermal growth factor receptor), responsible for tumor growth and cell proliferation. However, it will not work where other pathways are involved in prognosis of disease.

M-TORC1 (mammalian target of rapamycin-complexi) is disclosed in Karajannis M A et. al, Neuro Oncology 2014 January, 16(2):292-7. Karajannis M A et. al discloses phase II study of everolimus (mTOR inhibitor) to treat the neurofibromatosis type-2. mTORC1 (mammalian target of rapamycin-complexi) inhibits tumor initiation and increases apoptosis. However, it is specific to only for m-TORC1 pathway.

US20120157401 discloses vascular endothelial growth factor (VEGF) and its inhibitors. It inhibits pathological production of vascular endothelial growth factor to treat neurofibromatosis type-2. VEGF (vascular endothelial growth factor) inhibitors are effective to inhibit the angiogenesis in the tumor cells.

Inhibition of the Ras protein is disclosed by A. M. Tsimberidou et. al, Journal of Clinical Oncology, 2008 A.M. The tumor suppressor protein merlin (NF2) interferes with the activation of Ras and Rac. Ras protein inhibitors such as Salirasib inhibit the Ras activation that is used to prevent cell growth and proliferation.

S Ammoun et. al, in neuro-Oncology 2011 July, 13(7): 759-66 discloses a distinct pathway of neurofibromatosis type-2 treatment by inhibition of PDGFR (Platelet derived growth factor receptor). It discloses nilotinib alone or in combination with selumetinib as a drug candidate for neurofibromatosis type-2. Inhibition of platelet-derived growth factor receptor-β (PDGFR-β) leads to inhibition of extracellular-signal-regulated kinase (ERK1/2) and AKT/Protein Kinase B which prevents the schwannomatosis. However, PDGFR inhibitors again very specific and may not be effective for completely eradicating the tumor.

WO2007143630 discloses inhibition of HSP90 (Heat shock protein) for treating neurofibromatosis type-2 deficient or neurofibromatosis type-2 deficient cells with HSP90 inhibiting compound. HSP90 and/or up regulation of HSP70 is important for the proliferation and survival of NF2-deficient tumor cells. HSP90 inhibitors induce the proteasomal mediated degradation of the regulatory proteins such as kinases and transcription factors involved in proliferation, but there are many redundant factors involved in proliferation. Hence, it might not be an effective pathway for treatment of neurofibromatosis type-2.

All of the pathways discussed above have limitations and, no curative therapy or drug has been approved so far. Disease management relies almost entirely upon surgical removal of tumors. Hence, there is need to develop an effective method of treating neurofibromatosis type-2 and related conditions. The present invention is directed to overcoming these and other gaps in the art.

SUMMARY

It is a principal object of this invention to provide a method of treating tumors associated with cells having defective neurofibromatosis type-2 gene using a ubiquitin-proteasome system inhibitor.

A further aspect of the invention is to provide a method of diagnosis of patients having neurofibromatosis type-2 alteration-dependent tumors, the method comprises determining whether tumor cells have compromised activity of neurofibromatosis type-2/merlin protein due to defective neurofibromatosis type-2 gene and selecting deficient patients for treatment with an ubiquitin-proteasome system inhibitor.

Another aspect of invention is to provide a method of diagnosis and treatment of mesothelioma patient with a ubiquitin-proteasome system inhibitor, the method comprises diagnosis of patients suffering from mesothelioma and then finding whether the mesothelioma is associated with cells having a mutated neurofibromatosis type-2 gene, identifying patients as a neurofibromatosis type-2-dependent mesothelioma patient and administering to them a therapeutically active amount of ubiquitin-proteasome system inhibitor.

One another aspect of the invention provides a method of diagnosis of patients suffering from mesothelioma which is associated with cells in which the functional activity of merlin protein is absent due to a mutated BAP1 gene, identifying the patient as a BAP1 gene dependent mesothelioma patient and treating with a therapeutically active amount of ubiquitin-proteasome system inhibitor.

In a preferred aspect, the invention discloses use of bortezomib, a proteasome inhibitor for treating, preventing or ameliorating tumors or symptoms resulting from defective neurofibromatosis type-2 gene.

BRIEF DESCRIPTION OF FIGURES

FIG. 1: 20S Proteasome assay of bortezomib at conc. of 1 nM, 3 nM, 10 nM, 30 nM, 100 nM and 300 nM using carfilzomib as reference compound for 6 hrs incubation time.

FIG. 2: 20S Proteasome assay of bortezomib at conc. of 1 nM, 3 nM, 10 nM, 30 nM, 100 nM and 300 nM using carfilzomib as reference Compound for 12 hrs incubation time.

FIG. 3: 20S Proteasome assay of bortezomib at conc. of 1 nM, 3 nM, 10 nM, 30 nM, 100 nM and 300 nM using carfilzomib as reference Compound for 18 hrs incubation time.

FIG. 4: 20S Proteasome Assay of bortezomib at conc. of 1 nM, 3 nM, 10 nM, 30 nM, 100 nM and 300 nM using carfilzomib as reference Compound for 24 hrs incubation time.

FIG. 5: Percentage (%) inhibition of Proteasome activity of bortezomib at conc. of 1 nM, 3 nM, 10 nM, 30 nM, 100 nM and 300 nM in the NF2 knockout/wild type haploid cell line with 18 hrs incubation time interval.

FIG. 6: Caspase 3/7 activity for bortezomib at conc. of 0.1 nM, 1 nM, 3 nM, 10 nM, 30 nM, 100 nM and 300 nM in the NF2 knockout cell line. Staurosporine (1 & 10 µM) was used as a reference compound. Time intervals observed was 18 hrs.

FIG. 7: Caspase 3/7 activity for bortezomib at conc. of 0.1 nM, 1 nM, 3 nM, 10 nM, 30 nM, 100 nM and 300 nM in the wild type haploid cell line. Staurosporine (1 & 10 µM) was used as a reference compound. Time intervals observed was 18 hrs.

FIG. 8: Western Blot analysis for Bortezomib tested at conc. of 3 nM, 10 nM and 30 nM, in the NF2 knockout cell line (KO). Also shown is the wild type haploid cell line (WT) for LATS1 levels. UT: Untreated.

FIG. 9: Western Blot analysis blot for bortezomib tested at conc. of 3 nM, 10 nM and 30 nM (three lanes for each concentration) in the NF2 knockout (KO) cell line along with untreated (UN) NF2 knockout control and untreated wild type control with 18 hrs incubation. Also shown is the GAPDH (Endogenous Control) as standard control.

DETAILED DESCRIPTION

While this specification concludes with claims particularly pointing out and distinctly claiming that, which is regarded as the invention, it is anticipated that the invention can be more readily understood through reading the following detailed description of the invention and study of the included examples.

This invention, in general, relates to methods of inhibiting or reducing the growth of tumors associated with cells having neurofibromatosis type-2 gene mutation in patients comprises administering therapeutically effective amount of at least one ubiquitin-proteasome system inhibitor. The tumors may be a benign tumor or a malignant tumor having one or more mutations in the neurofibromatosis type-2 gene.

Neurofibromatosis type 2 is an autosomal dominant genetic trait, and it affects both genders equally and each child of an affected parent has a fifty percent chance of inheriting the gene. Neurofibromatosis type-2 results from a mutation or a deletion of the neurofibromatosis type-2 gene and is transmitted on chromosome 22. It is a tumor suppressor gene that encodes a 595-amino acid protein, termed merlin. Merlin belongs to the ezrin, radixin, and moesin (ERM) family of proteins. Merlin protein is also called as schwannomin or neurofibromin 2.

Neurofibromatosis Type-2 is characterized by growth of tumors in the nervous system. The most common tumors associated with neurofibromatosis type-2 are called vestibular schwannomas or acoustic neuromas, schwannomin, schwannomas of other cranial, spinal, and cutaneous nerves, as well as cranial and spinal meningioma.

Most of the time the tumor grows along the nerve that goes from the inner ear to the brain (the auditory nerve). Tumors that occur on other nerves are also commonly found with this condition.

The signs and symptoms of neurofibromatosis type-2 usually appear during adolescence or in a person's early twenties, although they can begin at any age. The most frequent early symptoms of vestibular schwannomas are hearing loss, ringing in the ears (tinnitus), and problems with balance. In most cases, these tumors occur in both ears by age 30. If tumors develop elsewhere in the nervous system, signs and symptoms vary according to their location. Complications of tumor growth can include changes in vision, numbness or weakness in the arms or legs, and fluid build-up in the brain. Tumors on the optic nerve can cause visual loss, on the gastrointestinal tract may cause bleeding or obstruction.

The mechanism by which loss of neurofibromatosis type-2 occur is still a subject matter of further research. However, researchers have focused both on genetic and biochemical approaches.

It is known that neurofibromatosis type-2 gene provides instructions for the production of a protein called merlin, also known as schwannomin. This protein is made in the nervous system, particularly in specialized cells that wrap around and insulate nerves (Schwann cells). Merlin is believed to play a role in controlling cell shape, cell movement, and communication between cells. To carry out these tasks, merlin associates with the internal framework that supports the cell (the cytoskeleton).

One of the most important functions of merlin is to function as a tumor suppressor. The tumor suppressor protein prevents cells from growing and dividing too fast or in an uncontrolled way. Merlin does this by translocating to nucleus and suppresses tumorigenesis through inhibition of $CRL4^{DCAF1}$, a protein complex belonging to the cullin ring family of E3 ligases. E3 ligases are integral part of the ubiquitin degradation pathway, catalysing the attachment of ubiquitin to a lysine on the target protein to be degraded, via an isopeptide bond. The inhibition of $CRL4^{DCAF1}$ leads to inhibition of proteasomal degradation of proteins involved in the downstream signalling (LATS1/2 kinases and YAP/TAZ) thereby activating the Hippo signalling pathway, a prominent anti-mitotic signalling mechanism of the cell which controls cell viability, proliferation and cell death. Dysfunction of Neurofibromatosis Type-2/merlin leads to its failure to inhibit $CRL4^{DCAF1}$ thereby deregulating the chain of events which activate the hippo signalling, eventually leading to development of schwannomas and meningioma associated with neurofibromatosis type-2, neurofibromatosis Type 5, schwannomatosis, benign meningioma, and cancer of the mesothelium (mesothelioma). Neurofibromatosis type-2 dependent tumorigenesis arises when mutant merlin cannot enter the nucleus and unable to suppress CRL4$^{DCAF1}$ dependent gene expression.

The ubiquitin-proteasome pathway is the central pathway for control of protein degradation of the intracellular proteins. Proteins are initially targeted for proteolysis by the attachment of a poly-ubiquitin chain, then rapidly degraded to small peptides by the proteasome and the ubiquitin is subsequently released and recycled. This coordinated proteolytic pathway is dependent upon the synergistic activity of the ubiquitin-conjugating system and the 26S proteasome. The 26S proteasome is a large, approximately 1500 to 2000 kDa, multi-subunit complex present in the nucleus and cytoplasm of eukaryotes. The catalytic core of this complex, referred to as the 20S proteasome, is a cylindrical structure consisting of four heptameric rings containing alpha and beta subunits. The proteasome is a threonine protease, the N-terminal threonine of the β-subunit providing the nucleophile that attacks the carbonyl group of the peptide bond in target proteins. At least three distinct proteolytic activities are associated with the proteasome: chymotryptic, tryptic and peptidylglutamyl. The ability to recognize and bind polyubiquinated substrates is conferred by 19S (PA700) subunits, which bind to each end of the 20S proteasome. These accessory subunits unfold substrates and feed them into the 20S catalytic complex, whilst removing the attached ubiquitin molecules.

In one of the embodiments, the present invention discloses a novel approach for treatment of neurofibromatosis type-2 schwannomas and meningiomas. The present inventors have established that disrupting ubiquitin-proteasome pathway has direct impact on molecular events downstream of the tumor suppressor neurofibromatosis type-2/merlin. The major impact of deficiency of neurofibromatosis type-2/merlin is dysregulation of proteasomes degradation, a proteasome inhibitor such as bortezomib can potentially nullify the effect of neurofibromatosis type-2/merlin deficiency by inhibiting the 26S proteasome and preventing the degradation of proteins involved in tumor suppression and activation of anti-mitotic pathways (e.g. hippo signalling).

In yet another embodiment, the present invention discloses the use of proteasome inhibitor such as but not limited to bortezomib for the treatment of neurofibromatosis type-2 and other conditions related to deficiency/dysfunction of neurofibromatosis 2/merlin, for example, mesothelioma, schwannomatosis, benign meningioma and neurofibromatosis type 5.

In a particular aspects, disclosed herein are methods of enhancing LATS activity in a tumor having compromised activity of neurofibromatosis type-2/merlin comprising administering bortezomib to a subject determined to having the tumor. In particular the the tumor is from a schwannoma. For example, the schwannoma may a vestibular schwannoma, a unilateral schwannoma, a bilateral vestibular schwannoma, a spinal cord schwannoma, a sporadic schwannoma, and a peripheral nerve schwannoma. Preferably, the bortezomib is subcutaneously administered to the subject having the tumor using prefilled syringe containing a formulation of bortezomib alone or in combination with steroid. In particular, aspects, the bortezomib is administered in an amount sufficient to increase LATS activity by at least 20%, at least 30%, at least 50%, at least 60%, at least 80%, at least 100%, or at least 150% compared to the activity in an untreated cell having compromised activity of neurofibromatosis type-2/merlin. Without being bound by theory, it is thought that increased LATS activity results in tumor cell killing.

Further, the present inventor come to know that activity of ubiquitin-proteasome pathway is high in neurofibromatosis type-2 deficient mesothelioma tumor.

In another embodiment, the present invention discloses a linkage between ubiquitin-proteasome pathway and mesothelioma, a rare form of cancer that develops from cells of the mesothelium, the protective lining that covers many of the internal organs of the body. Currently available therapies for mesothelioma have limited effect on outcomes. Even with aggressive multimodality therapy including surgery for early stage disease, the median overall survival is very short from the time of diagnosis.

Mutations of the neurofibromatosis 2 tumor suppressor gene cause the inherited disorder neurofibromatosis 2 and are also common in malignant mesothelioma, which is not a characteristic feature of the neurofibromatosis type-2 disease. Immuno histochemical analysis of the mesothelioma confirm loss of expression of neurofibromatosis type-2 protein, and comparative genomic hybridization revealed losses of chromosomes 14, 15, and 22, and gain of 7. The loss of NF2/merlin protein in mesothelioma tumors could accelerate tumor progression.

Bortezomib is a pharmaceutically active compound of formula [(1R)-3-methyl-1-({(2S)-3-phenyl-2[(pyrazin-2-yl carbonyl) amino]propanoyl}amino) butyl]boronic acid or pharmaceutically acceptable salts, derivatives, polymorph, racemate, conjugate, complex or stereoisomer thereof. Bortezomib is also referred to as (N-(2-pyrazine) carbonyl-L-phenylalanine-L-leucine boronic acid. It is believed that the boron atom in bortezomib binds to the catalytic site of the proteasome, ultimately leading to proteasome inhibition and reduced degradation of pro-apoptotic factors, which in turn triggers apoptosis in treated cells. Structurally, bortezomib is a boronated dipeptidic compound comprising L-leucine and L-phenylalanine moieties. Therefore, it comprises two chiral carbons and the molecule has rigid spatial orientation thus being a single diastereomer. It may form acid addition salts. In solid state, bortezomib is present in trimeric boroxine form. Various crystalline polymorphs of bortezomib have been described in the literature. See, for example, WO 2008075376 A1 discloses Form I polymorph of bortezomib and process for their preparation and WO 2014097306 A1 discloses Form N polymorph of bortezomib, Oxidized dextran-bortezomib-adriamycin conjugate medicine and its preparation method described in CN 104958769 A Boronic acid compound preparation containing block copolymer, method for its manufacture, and drug containing WO 2015002078 A1 20150108. In other aspects, Bortezomib is combined with D-gluconic acid to make the formulation more stable.

In yet another embodiment, the proteasome inhibitor of present invention also acts via mTORC1 pathway for the treatment of neurofibromatosis type-2. Neurofibromatosis type-2/merlin negatively regulates mammalian target of rapamycin (mTOR complex 1) and the deregulation of mTORC1 signalling activation underlies the aberrant growth and proliferation of neurofibromatosis type-2-associated tumors.

Yet another embodiment of the invention envisions the inhibition of Neurofibromatosis type 1 gene product neurofibromin by a proteasome inhibitor. Neurofibromin is a tumor suppressor protein that suppresses Ras function. Neurofibromin is dynamically regulated by the proteasome, and its degradation and re-expression are essential for maintaining appropriate levels of Ras-GTP. Neurofibromatosis type 1/neurofibromin could be activated in cancer by both mutations and excessive proteasomal mediated destruction. Proteasomal inhibitors like bortezomib is useful for regulation of neurofibromin.

In yet another embodiment, the present invention discloses that proteasome inhibitor is optionally combined with a steroidal drug, preferably dexamethasone for synergistic effect.

Drug Formulations

In general, inhibitors of the ubiquitin-proteasome system are formulated for administration in accordance with known techniques. See, e.g., *Remington, The Science and Practice of Pharmacy* (9th Ed. 1995).

It will be further appreciated by persons skilled in the art that the inhibitor of ubiquitin-proteasome system may be formulated at various concentrations, depending on a number of factors including the efficacy/toxicity of the inhibitor being used and the indication for which it is being used. The formulations should contain an amount of the inhibitor sufficient to provide in vivo concentration at or near the target tumor cells which is sufficient to induce their cell death (e.g. via apoptosis). The concentration or amount necessary to provide the desired effect depends on the potency of the inhibitor in question and can be established by methods known by a person skilled in the art or be already available information. The same applies to the daily dose and the dosage regime for the individual inhibitors.

The protostome inhibitor compounds of present invention could delivered by any means known in the prior art, including oral, internal, pulmonary, rectal, nasal, vaginal, lingual, transdermal, intravenous, intra-arterial, intramuscular, intraperitoneal, intra-tumoral, intracutaneous and subcutaneous routes.

The more preferred route is oral such as tablets, capsules or solution, topical, transdermal or by intra-tumoral injection. Subcutaneous route of delivery is most preferred route of delivery of a proteasome inhibitor alone or in combination with a steroidal drug, for the treatment of neurofibromatosis type-2 and associated tumors.

In yet another embodiment, the present invention provides that the bortezomib is administered subcutaneously and on the same time dexamethasone is given orally. Subcutaneous delivery is performed in the hypodermis (under the skin) generally as a short injection (few seconds or minutes). However, the volume of injection has to be limited (1-6 ml) for pain reasons, necessitating the use of concentrated formulations and sometimes two separate sites of administration.

The amount of proteasome inhibitor compound present in a composition should, in general, be in the range of about 0.01 to about 30% w/w and preferably in an amount of 1 to 20% w/w of composition. Proteasome inhibitor compound is preferably bortezomib.

In another embodiment, the present invention provide a pharmaceutical formulation comprises of an ubiquitin-proteasome system inhibitor in combination with pharmaceutically acceptable excipients(s). In yet an embodiment, the present invention provides a pharmaceutical composition for topical application. A topical pharmaceutical composition could be applied to the skin near neurofibromatosis type-2 deficient tumors. The topical formulation could be an ointment, cream, lotion, paste, gel, spray, aerosol, or oil. Carriers which are generally used to formulate a topical formulation are such as petroleum jelly, lanoline, polyethylene glycols, alcohols, transdermal enhancers, and combinations of two or more thereof.

In further embodiments, the present invention discloses that ubiquitin-proteasome system inhibitor compositions is a transdermal patch, adapted to remain in intimate contact with the epidermis of the patient for a prolonged period of time. The compositions are applied near or at the site of a neurofibromatosis type 2 deficient tumor. Transdermal formulation is delivered through iontophoresis and typically takes the form of an optionally buffered aqueous solution of the active compound. Suitable formulations comprise citrate or bis\tris buffer (pH 6) or ethanol/water and contain from 0.1 to 0.2M of active ingredient.

The present invention also discloses a method of treatment using a liposomal formulation of ubiquitin-proteasome pathway inhibitor and salts thereof. The technology for forming liposomal suspensions is well known in the art. When the inhibitor is water-insoluble, the salt may be substantially entrained within the hydrophobic lipid bilayer which forms the structure of the liposome. The liposomes which are produced may be reduced in size, as through the use of standard sonication and homogenization techniques. Of course, the liposomal formulations containing the ubiquitin-proteasome pathway inhibitor disclosed herein or salts, conjugate or complex thereof may be lyophilized to produce a lyophilizate which may be reconstituted with a pharmaceutically acceptable carrier, such as water, to regenerate a liposomal suspension. Preferred liposomal formulation of bortezomib comprises bortezomib and polyol, it further comprises hydrogen ion gradient, hydrophobic moiety (lipid) derivative with polyethylene glycol wherein bortezomib is entrapped in liposomes.

The inhibitors of the ubiquitin-proteasome system may also be administered intranasal or by inhalation and are conveniently delivered in the form of a dry powder inhaler or an aerosol spray presentation from a pressurised container, pump, spray or nebuliser with the use of a suitable propellant or a suitable gas.

Pharmaceutical compositions of the present invention suitable for parenteral administration comprise sterile aqueous and non-aqueous injection solutions of the active compound, where preparations are preferably isotonic with the blood of the intended recipient. These preparations may contain anti-oxidants, buffers, bacteriostats and solutes which render the formulation isotonic with the blood of the intended recipient. Aqueous and non-aqueous sterile suspensions may include suspending agents and thickening agents. One of the preferred parenteral formulation comprises of bortezomib compound or its derivatives, salts, polymorphs or isomers, conjugate or complex thereof with tromethamine in a molar ratio of 1:3 and pH is adjusted in the range of 3-6.5 and the composition is in the freeze dried form. More preferably, pH is adjusted in the range of 4-5.

Bortezomib could also be formulated as sterile lyophilized mixture with mannitol. Preferred, injectable lyophilized composition comprises water for injection subjected to nitrogen purging, bortezomib is dissolved in tert-butanol, and moisture content of lyophilized formulation is 3.5-6.5%. One another embodiment discloses an injectable liquid formulation comprises of bortezomib and tartaric acid in the ratio of 2:1 and pharmaceutically acceptable carrier.

In another embodiment, the present invention discloses a liquid formulation comprising a non-aqueous solvent propylene glycol, bortezomib and buffer agent of pH 3 to 4. In one of the embodiment, the present invention discloses a solid formulation comprising boric acid, bortezomib and glycine. In one another aspect, the invention provides a composition that includes only bortezomib and boric acid. The composition is a solid, and the mass ratio of boric acid to bortezomib is from 1:1 to 10:1. In certain aspects, bortezomib is provided in the monomeric boronic acid form in water at 3.3 to 3.8 mg/ml in a pH range of 2 to 6.5.

Bortezomib sustained release formulation as a nanomaterial or nano drug carrier comprises of carbon quantum dots, chitosan nanoparticles and bortezomib.

In one of the embodiments, the present invention also discloses a composition for applying directly at the site of neurofibromatosis type-2 deficient tumors. For instance, the proteasome inhibitor can be applied by local treatment which encompasses both topical treatment and intralesional or intradermal treatment at the site of the tumor. Therefore, the inhibitor can be injected into, topically applied onto or near neurofibromatosis type-2 deficient tumors. In one embodiment of the invention, the inhibitor is applied intralesionally by methods known in the art. Alternatively, pharmaceutical composition of a proteasome inhibitor can take the form of an implant. Such a composition can be surgically implanted at or near the site of a tumor for slow release of the inhibitor.

In another preferred embodiment, the present invention discloses containers including an ampoule, a vial, a pre-filled syringe, and intravenous bag. Preferred multi-use containers will contain bortezomib alone or in combination with additional drug such a steroid in an amount suitable to allow at least two distinct uses, more typically at least five, and most typically at least ten distinct uses (each of which may or may not require the same quantity of formulation administered to the patient).

In yet another embodiment, the present invention provides a device for disc shunt implantation and peri-shunt injection comprising bortezomib formulation alone or in combination with another drug.

In another embodiment, the present invention discloses a companion diagnostic kit based on genetic testing, in order to screen patients of neurofibromatosis type-2, mesothelioma, schwannomatosis, benign meningioma and/or neurofibromatosis type 5 for mutations in the neurofibromatosis type-2/merlin gene.

It is known that every case of schwannomatosis and mesothelioma is not related to neurofibromatosis type-2/merlin mutation. The activity of the ubiquitin-proteasome pathway is found to be high in 30% to 40% of mesotheliomas patients. However, the cause of remaining 60% cases of mesothelioma is found to be different. Hence, the ubiquitin-proteasome pathway inhibitor of present invention may not be effective in 60% of mesotheliome cases. Hence, it is necessary to first segregate patients having mesothelioma associated with neurofibromatosis type-2/merlin gene mutation. The present invention discloses a companion diagnostic kit based on genetic analysis or immuno-histochemistry in order to screen mesothelioma patients dependent on for neurofibromatosis type-2/merlin gene mutation. In one another embodiment, the present invention discloses administering the therapeutically effective amount of an ubiquitin-proteasome pathway inhibitor to such patients.

In yet another embodiment, the present invention discloses a method of genetic testing which may include deletion/duplication analysis, sequence analysis of select exons, sequence analysis of the entire coding region, linkage analysis, mutation scanning of the entire coding region, deletion/duplication analysis. Smaller deletions that remove multiple exons of neurofibromatosis type-2/merlin or the whole gene can also be identified by FISH (Fluorescence in situ hybridization) analysis.

In yet another embodiment, the present invention discloses a method of identifying and treating a suspect of mesothelioma patient for whom administration of an inhibitor of ubiquitin-proteasome system would be therapeutically beneficial, the method comprises first diagnosing whether patient is suffering from mesothelioma and if yes then ascertaining diagnosed mesothelioma association with cells in which the functional activity of merlin protein is absent due mutated BAP1 gene, identifying the patient as a BAP1 gene dependent mesothelioma patient and administering a therapeutically active amount of ubiquitin-proteasome system inhibitor. BAP1 (BRCA1-Associated Protein 1) associated protein-1 (ubiquitin carboxy-terminal hydrolase) is a 729 amino acid nuclear ubiquitin hydrolase. This gene belongs to the ubiquitin C-terminal hydrolase subfamily of deubiquitinating enzymes that are involved in the removal of ubiquitin from proteins. BAP1 has been shown to induce cell death by a process with similarities to both apoptosis and necrosis. Additionally, BAP1 regulates cell proliferation by deubiquitinating host cell factor-1 (HCF-1), 25 a chromatin-associated protein believed to activate and repress transcription by linking appropriate histone modifying enzymes to a subset of transcription factors, in particular of the E2F family. BAP1 encodes for an ubiquitin C-terminal hydrolase (deubiquitinase, DUB) and is therefore able to reverse the ubiquitin linkages formed by E3 ubiquitin ligases.

In one embodiment, the invention provides a method of killing tumor cells associated with neurofibromatosis type-2 gene mutation comprising administering an amount of a proteasome inhibitor. A non-limiting exemplary proteasome inhibitor is bortezomib.

In another embodiment the present invention discloses that tumor associated with neurofibromatosis type-2 is a vestibular schwannoma, an acoustic neuroma, a unilateral schwannoma, a bilateral vestibular schwannoma, a spinal cord schwannoma, a sporadic schwannoma, a peripheral nerve schwannoma, a meningioma, a mesothelioma, an ependymoma, a glioma and an astrocytoma. In particular embodiments, the NF-2 deficient tumor cells are not meningiomas.

In one another embodiment, the present invention discloses that the inhibitor of the ubiquitin-proteasome system is a proteasome inhibitor acting directly upon the proteasome to inhibit its function. For example, the proteasome inhibitor may inhibit (at least, in part) the ability of the human proteasome to degrade proteins. The inhibitor of the ubiquitin-proteasome system may also be an ubiquitin inhibitor and include ubiquitin ligase inhibitor, ubiquitin specific peptidase 8 (USP8) inhibitor, ubiquitin-like modifier activating enzyme 3 (UBA3) inhibitor, ubiquitin-specific protease 7 (USP7) inhibitor.

In one another embodiment, the present invention discloses that the inhibitor of ubiquitin-proteasome system is a proteasome inhibitor which could be a molecules under development or any antibody and are selected from group consisting of bortezomib, carfilzomib, CEP28331, Proteasome inhibitor ONX-0914, VL01, E18770, Ixazomib citrate (MLN9708), NPI-0052 (salinosporamide A), HCV proteasome inhibitor, HIV Proteasome Inhibitor, KRX-040 (perifosine), MLN-273, MLN-519 (formerly known as LDP-519), tetra-acridines, MLN4924 (inhibitor of NEDD8), HBX19818, HBX41108 (USP7, protease 7 Inhibitors), ubiquitin ligases, USP8 Inhibitors (cysteine-proteases), CC12507, HBX99200 and P5091.

More specifically, the inhibitor of the ubiquitin-proteasome system is a proteasome inhibitor selected from the group consisting of bortezomib (PS-341, MG-341, Velcade®), PI-083, MLN 9708, MLN 4924, MLN 519, carfilzomib, ONX 0912, CEP-1877, NPI-0047, NPI-0052, BU-32

(NSC D750499-S), PR-171, IPSI-001, and natural products with proteasome-inhibitory effects, such as green tea polyphenol (−)-epigallocatechin-3-gallate (EGCG), soy isoflavone genistein, and the spice turmeric compound curcumin. Most preferably, proteasome inhibitor is a bortezomib.

The invention also provides a method of treating neurofibromatosis type-2 using a substance that interferes with the activity of CUL4A such as 1,3-benzoxathiol-2-one compound, a pyridinethione compound, or a 2,6-diamino-4-thiopyran-3,5-dicarbonitrile. The gene encoding the CUL4A ubiquitin ligase (also referred to in the art as Cullin Ring Ligase 4 (CRL4) and Cullin-4A) is frequently amplified or overexpressed in a wide variety of cancer types where neurofibromatosis type-2/merlin gene mutation is reason for over expression of Cullin Ring Ligase 4, such as breast cancer or primary malignant pleural mesothelioma.

In yet another embodiment, the present invention discloses that the inhibitor of ubiquitin-proteasome system is normally administered at a dose in range of between 0.01 to 100 mg/m$^2$ per dose such as between 0.5 to 1.3 mg/m$^2$ per dose, which may be repeated at regular intervals (for example daily, twice weekly, weekly, bi-weekly, monthly, etc.). Preferably, inhibitor of ubiquitin-proteasome system is bortezomib which is administered to patients in a dose range of 0.1 mg per day to 50 mg per day. More preferably, dose of 1 mg per day to 10 mg per day. Most preferably, bortezomib is given to patients in a dose of about 1.3 mg/m$^2$ via intravenous bolus for 3 to 5 seconds, twice in a week for at least 2 weeks (days 1, 4, 8 and 11) of a 21-days cycle for up to eight cycles.

In one of the embodiments, the inhibitor of the ubiquitin-proteasome system is formulated in various concentrations. For example, the pharmaceutical formulation may comprise a proteasome inhibitor at a concentration of between 1 µM and 1 mM, for example between 1 µM and 100 µM, between 5 µM and 50 µM, between 10 µM and 50 µM, between 20 µM and 40 µM or about 30 µM.

In yet another embodiment, the present invention discloses that the dose of bortezomib in range of 1 mg/m$^2$ to 2.6 mg/m$^2$ may be delivered subcutaneously through the abdomen or the thigh. Back of the arm can also be considered as a third option. Preferable schedule is twice per week for neurofibromatosis type-2 patients. Subcutaneous administration of bortezomib significantly reduces the occurrence of peripheral neuropathy. Bortezomib dilution for both the subcutaneous route and intravenous route is the same and may result in a 1 mg/ml concentration.

In yet another embodiment, the present invention discloses a formulation comprising dexamethasone and bortezomib for treatment neurofibromatosis type-2. Preferable dose of dexamethasone is in range of 5 mg to 40 mg daily alone or in combination with bortezomib. Preferred routes are oral, intravenous and subcutaneous delivery.

In the preferred embodiment, the present invention discloses a method of treating a patient having malignant or non-malignant tumor, wherein said tumor cells have one or more mutations in the neurofibromatosis type-2 gene, comprises administering to said patient a therapeutically effective amount of a proteasome inhibitor.

In another preferred embodiment, the present invention discloses a method of diagnosis of neurofibromatosis type-2 dependent tumor patients. The method comprises determining whether the tumor cells have compromised activity of neurofibromatosis type-2/merlin due to defective neurofibromatosis type-2 gene and treating with a ubiquitin-proteasome system inhibitor.

In yet another preferred embodiment, the present invention discloses method of identifying a mesothelioma patient for whom administration of an inhibitor of the ubiquitin-proteasome system would be therapeutically beneficial, the method comprises: a) determining whether the mesothelioma cells have mutated neurofibromatosis type-2 gene; and b) wherein the mesothelioma is found in step (a) to be associated with cells in which the functional activity of merlin protein is absent due mutated neurofibromatosis type-2 gene, identifying the patient as a neurofibromatosis type-2 dependent mesothelioma patient and treating with a therapeutically effective amount of a ubiquitin-proteasome system inhibitor. Preferably, inhibitor of the ubiquitin-proteasome system is a proteasome inhibitor.

In a further preferred embodiment, the present invention discloses a method of treating or preventing tumors or symptoms resulting from defective neurofibromatosis type-2 gene in a subject comprise diagnosing patients by obtaining from said patient a biological sample for diagnosis of neurofibromatosis type-2 gene mutation and selecting such patients for administering an effective amount of ubiquitin-proteasome system inhibitor.

In another embodiment, disclosed herein is the use of bortezomib or its derivatives or salts polymorphs or isomers thereof for inhibiting or reducing the growth or number of neurofibromatosis type-2 deficient tumor cells. Advantageously, the treatment of neurofibromatosis type-2 deficient tumor cells results in the stimulation of apoptosis, leading to a reduced tumor size. Without being bound by theory, it is as though bortezomib mimics the effect of merlin/NF-2 protein in patients having tumors caused by deficiency of merlinNF-2 protein.

In one another embodiment, the present invention suggests that ubiquitin-proteasome system inhibitors could be used in parallel to additional treatment wherein another pharmaceutical agent, radiotherapy and/or surgery is used/performed for treatment of neurofibromatosis type-2/merlin.

The further treatments are selected from the group consisting of conventional chemotherapeutic agents (such as alkylating agents, anti-metabolites, plant alkaloids and terpenoids, topoisomerase inhibitors and antineoplastics), radiotherapeutic agents, antibody-based therapeutic agents (such as gemtuzumab, alemtuzumab, rituximab, trastuzumab, nimotuzumab, cetuximab, bevacizumab) and steroids.

Steroids are hormones naturally produced in the body. Steroids are used to treat diseases. When two different drugs have complementary mechanisms of action they work in different ways, but when given together, can be more effective at inhibiting the disease.

In yet another embodiment, the present invention discloses that the steroids are combined with bortezomib to provide a synergistic improvement in response for the treatment of neurofibromatosis type-2, vestibular schwannomas, acoustic neuromas, unilateral schwannoma, bilateral vestibular schwannomas, spinal cord schwannomas, sporadic schwannomas, peripheral nerve schwannomas, meningioma, mesothelioma, ependymoma, glioma and astrocytoma.

In the most preferred embodiment, the present invention discloses the use of a proteasome inhibitor for treating, preventing or ameliorating tumors or symptoms resulting from defective neurofibromatosis type-2 gene in human beings.

In yet another embodiment, the present invention discloses a method of a diagnosis and treatment of patients suffering from mesothelioma, where defective gene of neurofibromatosis type-2 and BAP1 are responsible for mesothelioma using a proteasome inhibitor. Mesothelioma, or malignant pleural mesothelioma (MPM), patients are diagnosed by pleural biopsy and diagnostic markers. Pleural biopsy is preferentially done by thoracoscopy to obtain tissue samples from the lungs in order to diagnose mesothelioma. Markers for the diagnosis of mesothelioma are calretinin, podoplanin, WT1 and cytokeratin 5/6. About 35-40% of mesothelioma patients carry inactivating mutations in the neurofibromatosis-2 (NF2) gene which encodes the protein Merlin. A significant percentage of patients also carry mutations in the BAP1 (BRCA associated protein 1) gene. Both of these populations are non-overlapping, which means that no patient has mutation in both the genes. Mesothelioma patients can be screened for mutation(s) in any of these genes by molecular genetic testing, which is done by the mutation scanning and gene duplication/deletion testing. For example, mutation scanning is done by polymerase chain reaction amplification of the DNA of patients compared to control DNA, and DNA with altered DNA segments may be subjected to the further testing, such as sequence analysis to identify the sequence alterations. Gene duplication/deletion testing is done by quantitative polymerase chain reaction, long-range polymerase chain reaction, multiplex ligation-dependent probe amplification (MLPA), and chromosomal microarray (CMA) that includes the gene/chromosome segment for detection. Molecular genetic testing confirms about the mutation in the NF2 gene or that in the BAP1 gene. Mesothelioma patients once confirmed to be carrying mutations in either of the two (NF2 or BAP1) genes are treated with bortezomib. Bortezomib at a dose of 1.3 mg/m$^2$ via intravenous bolus for 3 to 5 seconds is given to patients, twice in a week for at least 2 weeks (days 1, 4, 8 and 11) of a 21-d cycle for up to eight cycles. Patient shows marked improvement in terms of decrease in tumor progression as well as decrease in tumor size. A delay of 50% in tumor progression and 25% reduction in tumor size is noted.

The disclosed embodiments are not intended as limiting and alternative or additional embodiments may be provided.

Definitions

A "proteasome inhibitor" refers to a compound that blocks the action of proteasomes, i.e. cellular complexes that break down proteins, such as for example the p53 protein. Several classes of proteasome inhibitors are known. The class of the peptide boronates includes bortezomib and peptide boronate (CEP-18770). Other classes of proteasome inhibitors include peptide aldehydes (e.g. MG132), peptide vinyl sulfones, peptide epoxyketones (e.g. epoxomicin, carfilzomib), β lactone inhibitors (e.g. lactacystin, MLN 519, NPI-0052, Salinosporamide A), compounds which create dithiocarbamate complexes with metals (e.g. disulfuram, a drug which is also used for the treatment of chronic alcoholism), and certain antioxidants (e.g. Epigallocatechin-3-gallate) catechin-3-gallate, and Salinosporamide A.

As used herein, the term "subject or "patient," used interchangeably, means any animal, including mammals, such as mice, rats, other rodents, rabbits, dogs, cats, swine, cattle, sheep, horses, or primates, such as humans.

As used herein, the term about means + or −10% of the indicated value.

By "inhibitor of the ubiquitin-proteasome system" we mean an agent, such as a small chemical entity, polypeptide or the like, which is capable of inhibiting (at least, in part) a function of the ubiquitin-proteasome system (preferably in vivo in humans). Such an inhibitor may act at any point along the ubiquitin-proteasome protein degradation pathway, for example by inhibiting (at least, in part) the marking of proteins for degradation by modulating ubiquitination or de-ubiquitination, by inhibiting the ability of the proteasome to recognize or bind proteins to be degraded, and/or by inhibiting the ability of the proteasome to degrade proteins.

The inhibitor of the ubiquitin-proteasome system will be administered to a patient in a pharmaceutically effective dose. A 'therapeutically effective amount', or 'effective amount', or 'therapeutically effective', as used herein, refers to that amount which provides a therapeutic effect for a given condition and administration regimen. This is a predetermined quantity of active material calculated to produce a desired therapeutic effect in association with the required additive and diluents, i.e. a carrier or administration vehicle. Further, it is intended to mean an amount sufficient to reduce and most preferably prevent a clinically significant deficit in the activity, function and response of the host. Alternatively, a therapeutically effective amount is sufficient to cause an improvement in a clinically significant condition in a host. As is appreciated by those skilled in the art, the amount of a compound may vary depending on its specific activity. Suitable dosage amounts may contain a predetermined quantity of active composition calculated to produce the desired therapeutic effect in association with the required diluents. In the methods and use for manufacture of compositions of the invention, a therapeutically effective amount of the active component is provided. A therapeutically effective amount can be determined by the ordinary skilled medical worker based on patient characteristics, such as age, weight, sex, condition, complications, other diseases, etc., as is well known in the art. The administration of the pharmaceutically effective dose can be carried out both by single administration in the form of an individual dose unit or else several smaller dose units and also by multiple administrations of subdivided doses at specific intervals. Alternatively, the dose may be provided as a continuous infusion over a prolonged period.

Example 1

In Vitro Analysis for the Evaluation of Bortezomib in NF2 Knockout Cell Line 1293-1 in Comparison to Control HAP1 Cell Line for Varying End Points.

An in vitro analysis of bortezomib was carried out in NF2 knockout cell line 1293-1 along with control HAP1 (haploid) wild type cell line (Horizon Genomics) with varying end points. This cell line serves as model for all NF2-deficient cells, as the first exon of the NF2 gene in this cell line has been deleted. Bortezomib was procured from Natco Pharma Limited and standard chemicals for assays such as Triton X-100 procured from Sigma, carfilzomib was procured from Selleckchem and Caspase 3/7 inhibitor, Staurosporine was procured from BPS Biosciences.

1.1. Evaluation of the Cell Proliferation/Cytotoxicity in the Nf2 Knockout and Control HAP1 (Haploid) Cell Line Using Bortezomib The NF2 knockout cell line 1293-1 and haploid (HAP1) cell line were maintained in their respective media supplemented with 10% FBS (Fetal Bovine Serum) and antibiotic, with a media change every 2-3 days till 80% confluency was attained. Sub-culturing of the cells was carried out by using 0.25% trypsin-EDTA solution. The cells were treated with trypsin and seeded into 96 well-clear bottom plates as per the desired cell number in 100 μL of media and allowed to adhere overnight. Compound dilutions were made and 100

µL of each concentration was added to the appropriate wells. Cells were incubated at 37° C./5% $CO_2$ for 6, 12, 18 and 24 hours and at different test concentrations ranges from 0.1 nM to 100 nM (i.e. 0.1, 0.3, 1, 3, 10, 30, 60 and 100 nM). Vehicle or negative control were cells without compound or appropriate controls for solvent system to be employed wherever applicable (cells were treated with Triton X-100). Cell proliferation was determined by using "MTS-based cell titer 96 aqueous One Cell Proliferation assay" (MTS Cell proliferation assay kit (Abcam, Cat # ab197010)) or CellTitre Blue fluorescence based method whereby absorbance measured was inversely proportional to the cytotoxicity. The detection was carried out at 750 nm with the help of Flex Station 3 (Molecular Devices) instrument.

The following tables shows results of the cell proliferation assay performed in the NF2 knockout cell line (Table 1) and HAP1 (haploid) cell line (Table 2)

TABLE 1

| S. No. | Conc. (nM) of bortezomib | Average % Cytotoxicity in the NF2 knockout cells | | | |
|---|---|---|---|---|---|
| | | 6 hrs | 12 hrs | 18 hrs | 24 hrs |
| 1 | 100 | 10.89 | 15.71 | 39.72 | 45.16 |
| 2 | 60 | 16.44 | 16.07 | 38.70 | 43.98 |
| 3 | 30 | 14.05 | 17.18 | 35.71 | 37.83 |
| 4 | 10 | 8.10 | −11.84 | 14.52 | 29.86 |
| 5 | 3 | −0.78 | −24.79 | −19.23 | −68.56 |
| 6 | 1 | −1.49 | −28.42 | −25.10 | −66.58 |
| 7 | 0.3 | −5.03 | −32.20 | −26.59 | −71.10 |
| 8 | 0.1 | −5.18 | −21.57 | −16.92 | −63.43 |

TABLE 2

| S. No. | Conc. (nM) of bortezomib | Average % Cytotoxicity in the wild type haploid (HAP1) cells | | | |
|---|---|---|---|---|---|
| | | 6 hrs | 12 hrs | 18 hrs | 24 hrs |
| 1 | 100 | 6.08 | 26.85 | 32.69 | 78.91 |
| 2 | 60 | 9.63 | 31.95 | 31.03 | 77.43 |
| 3 | 30 | 7.63 | 24.92 | 26.34 | 74.99 |
| 4 | 10 | 0.99 | 5.12 | 7.56 | 44.78 |
| 5 | 3 | 1.58 | 1.10 | 7.83 | 16.63 |
| 6 | 1 | 5.65 | 0.20 | 5.78 | 10.92 |
| 7 | 0.3 | 4.70 | 2.62 | 6.90 | 11.39 |
| 8 | 0.1 | 2.64 | 3.91 | 6.83 | 11.24 |

Conclusion: Bortezomib at concentration ranging from 0.1 nM to 100 nM do not show any significant cytotoxicity at 6 hrs and 12 hrs (10-15%) in the NF2 knockout cell line; however slight toxicity was observed at higher concentration (>30 nM) of bortezomib at 18 hrs and 24 hrs. In the wild type haploid (HAP1) cell line, Bortezomib did not show any significant toxicity at 6 hrs, however toxicity was observed at higher concentration (>30 nM) at 12, 18 & 24 hrs.

1.2. Evaluation of 20S Proteasome Activity in the Nf2 Knockout and Control HAP1 (Haploid) Cell Line Using Bortezomib The NF2 knockout cell line 1293-1 and haploid (HAP1) cell lines were seeded in 6 well plates. The cells were then washed in PBS (Phosphate buffered saline) and lysed in a buffer containing non-ionic detergent and ATP. The cell lysate was centrifuged at 15,000 g for 30 minutes at 4° C. The supernatant was collected, aliquoted and stored at −80° C. until assay. Chymotrypsin-like peptidase activity of 20S proteasome was measured by using 40 µM Succinyl-Leu-Leu-Val-Tyr-AMC (Boston Biochem: S-280), a fluorogenic peptide substrate, along with 12 nM of recombinant PA28α (Boston Biochem: E-381 or R&D Systems Cat. # E-381-100), in an assay buffer containing 20 mM HEPES pH 7.4 and 0.5 mM EDTA. 20S proteasome cleaved the peptide substrate to release the free fluorophore AMC. NF2 knockout cells were incubated at 37° C./5% $CO_2$ for 6, 12, 18 and 24 hours and at 6 different test concentrations of bortezomib ranging from 1 nM to 300 nM (i.e. 1 nM, 3 nM, 10 nM, 30 nM, 100 nM and 300 nM). The controls were vehicle or negative control (NF2 cells without compound or appropriate controls for solvent system to be employed wherever applicable). The compound carfilzomib was used as an internal control for the assay (NF2 cells treated with carfilzomib). Similar assay was also performed with the wild type haploid (HAP1) cells for 18 hrs at different bortezomib concentrations ranging from 1 nM to 300 nM (i.e. 1 nM, 3 nM, 10 nM, 30 nM, 100 nM and 300 nM). The reaction was monitored by measuring the fluorescence through Flex Station 3 (Molecular Devices) or Envision (PerkinElmer) (excitation/emission: 353/442 nm), for 1 hour a 37° C. under kinetic setting. Substrate turnover was estimated as a standard curve generated using standard AMC. The results of 20S proteasome assay are described in FIGS. 1, 2, 3, 4 & 5.

Conclusion: Bortezomib showed dose dependent decrease in proteasome activity from 1 nM to 300 nM concentration in the NF2 knockout cell line. Proteasome activity decreased significantly with bortezomib from 3 nM onwards concentration post 6 hrs, 12 hrs, 18 hrs and 24 hrs incubation. Bortezomib also showed inhibition in proteasome activity in the wild type haploid cell line in a concentration dependent manner at 18 hrs. A comparison of the % inhibition in the proteasome activity post 18 hrs incubation with bortezomib (FIG. 5) demonstrated greater inhibition in the NF2 knockout cells when compared to the wild type haploid cells.

1.3. Evaluation of Caspase 3/7 Activity in the NF2 Knockout and Control HAP1 (Haploid) Cell Line Using Bortezomib Cultured NF2 knockout cell line 1293-1 cells and control Haploid cells (control wild type cells) were seeded in 96 well plates. 5 µl/well of bortezomib at different concentrations was added and incubated at 37° C./5% $CO_2$ for 18 hrs and at different test concentrations of 0.1 nM to 300 nM. Vehicle or negative control were cells without compound or appropriate controls for solvent system to be employed wherever applicable and positive control was cells were treated with Staurosporine). Caspase 3/7 activity in the cell lysate supernatants was estimated using a homogeneous and sensitive luminescent assay. Caspase-Glo® 3/7 Assay kit (Promega Cat # G8093) contains a substrate with tetrapeptide sequence DEVD selective for Caspase3/7 activity. Caspase activity cleaves the substrate and liberates free aminoluciferin, which in turn acts as a substrate for luciferase, generating luminescent signal. The luminescent signal is directly proportional to the activity of caspase 3/7. The luminescent signal is measured in the TopCount (PerkinElmer) or Envision (PerkinElmer) instrument. Appropriate negative controls and Staurosporine as a reference inhibitor were included in every assay.

Result: A significant increase in the caspase activity (apoptosis) was observed in the presence of bortezomib at different concentrations (3 nM onwards) in the NF2 knockout cell line. However, in the control haploid cells, minimal increase in apoptosis/Caspase 3/7 activation occurs at 18 hrs at varying concentrations (3 nM onwards) compared to NF2 knockout cell line (FIGS. 6 & 7). Staurosporine induced apoptosis was also observed in the Caspase 3/7 assay which served as a positive reference control in both cell lines. The concentrations at which increase in apoptosis/caspase activation is obtained are the similar concentrations at which proteasome inhibition is observed in NF2 knockout cells in the proteasome assay. The increase in apoptopic activity signifies the potential for shrinkage of NF2 tumors due to bortezomib treatment.

1.4. Western Blot Analysis for LATS1 Protein in the Nf2 Knockout and Control HAP1 (Haploid) Cell Line after Incubation with Bortezomib Cells from NF2 knockout cell line 1293-1 cells control Haploid cell line (control wild type cells) are seeded in 6 well plates. Cells were incubated at 37° C./5% $CO_2$ for 18 hours at different test concentrations i.e. 3, 10 & 30 nM of bortezomib. LATS1 protein was assayed by Western blot (Chemiluminescence) method and both NF2 cell lines are used in the analysis. Vehicle or negative control were cells without compound or appropriate controls for solvent system to be employed wherever applicable. Cell lysates were analysed by western blotting and LATS1 was detected using anti-lats1 antibody (Abcam, ab70561); GAPDH protein levels were assayed using anti-GAPDH antibody as endogenous control. The objective was to quantify the up-regulation/down-regulation of proteins (LATS1) involved in Hippo signaling pathway in NF2 knockout cell line compared to the control cell line. Another objective is to observe the effect of bortezomib treatment in the NF2 knockout cell line, following assays using the Western Blot/WES System.

Results: The relative levels of LATS1 protein was assayed after 18 hrs of treatment with bortezomib in control Haploid cell line (control wild type cells) and NF2 knockout cell line 1293-1 (FIGS. 8 and 9). In control haploid cells, there is greater expression of LATS1 (which signifies phosphorylation of YAP1), resulting from the inhibition of the ubiquitination process by the NF2 protein. In comparison in the NF2 knockout cells, there is very less expression of LATS1 (signifying less phosphorylated YAP1) as compared to control haploid cell line. This is due to lack of functional NF2 protein resulting in ubiquitination and degradation of LATS1. Treatment of NF2 knockout cell line with bortezomib at 3, 10 & 30 nM at 18 hrs showed increased levels of LATS1 (signifying increase in phosphorylated YAP1) with increasing bortezomib concentrations as compared to the cells not treated with bortezomib, demonstrating the rescue of LATS1 by inhibiting proteasome mediated degradation (FIGS. 8 & 9). Thus treating NF2 knockout cell lines with bortezomib rescues LATS1 protein from proteasome mediated degradation and the resulting function of LATS1 (phosphorylation of YAP and activation of the hippo pathway) results in inhibiting proliferation in NF2 knockout cells. Concomitant increase in apoptosis seen due to bortezomib treatment in NF2 knockout cell lines clearly demonstrate the utility of using bortezomib to stop proliferation and even potential reduction in size of of NF2 tumors.

All of the above results: the decrease in proteasome activity, increase in cytotoxicity and rescue of the hippo pathway in NF2 knockout cells by bortezomib treatment clearly demonstrates the therapeutic utility of bortezomib in treating NF2 tumors, including schwannomas and meningiomas.

Example 2

Formulation of Bortezomib and Dexamethasone

A suitable quantity of propylene glycol is fed into a manufacturing vessel and subsequently the required quantity of alcohol is added. The two components are then mixed. Nitrogen is then purged into the solution obtained in the previous step until the oxygen content is below 7 mg/l, preferably below 3 mg/l. Bortezomib and Dexamethasone is added and stirred in about 80% of the solution obtained in the previous step and dissolved. The volume is then made up to 100% with the solution obtained in step 2. The resulting drug solution is then filtered through a suitable sterilizing grade filter and filled into vials. The vial headspace is then blanketed with nitrogen to achieve a headspace oxygen content of less than 10%, preferably less than 5%, more preferably less than 2%. Finally the vials are stoppered and sealed.

The stability profile of the formulation according example 3 was analysed and is presented in Table 8 and 9. The amount of drug in the composition was measured before and after storage. The term "assay" as used in table 8 and 9 refers to the quantitative determination of drugs via HPLC. Also, the impurity profile of the composition was analysed before and after storage at various temperature and humidity conditions.

TABLE 3

| S. No. | Ingredients | Quantity (mg/ml) |
|---|---|---|
| 1 | Bortezomib | 2 mg |
| 2 | Dexamethasone | 20 mg |
| 3 | Propylene glycol | 1.6 ml |
| 4 | Tocopherol | 0.05% w/v |
| 5 | Ethanol | q.s. to 2 ml |

Example 3

Prefilled Syringe Formulations with Bortezomib

Examples of compositions for prefilled-syringe of bortezomib for parenteral administration are disclosed below. The examples are intended to be illustrative and not limiting.

TABLE 4

| S. No. | Ingredients | Quantity |
|---|---|---|
| 1 | Bortezomib | 3.5 mg |
| 2 | Polyvinylpyrrolidone (PVP) | 15 mg |
| 3 | Mannitol | 35 mg |
| 4 | Benzyl Alcohol | 1-2% w/v |
| 5 | Tocopherol | 0.05% w/v |
| 6 | Tetra Acetic Acid | 0.05% w/v |
| 7 | Sodium chloride | 0.9% w/v |
| 8 | Sodium Hydroxide | q.s. to adjust pH |
| 9 | Water for injection | q.s. to makeup the volume |

TABLE 5

| S. No. | Ingredients | Quantity |
|---|---|---|
| 1 | Bortezomib | 3.5 mg |
| 2 | Cyclodextrin | 15 mg |
| 3 | Benzyl Alcohol | 1-2% w/v |
| 4 | Butylated hydroxytoluene | 0.0001% w/v |
| 5 | Butylated hydroxyanisole | 0.0001% w/v |
| 6 | Sodium chloride 0.9% | q.s. make isotonic solution |
| 7 | Sodium Hydroxide | q.s. to adjust pH |
| 8 | Water for injection | q.s. to makeup the volume |

TABLE 6

| S. No. | Ingredients | Quantity |
|---|---|---|
| 1 | Bortezomib | 3.5 mg |
| 2 | Polyethylene glycol 400 | 2 ml |

TABLE 6-continued

| S. No. | Ingredients | Quantity |
|---|---|---|
| 3 | Polysorbate 20, | 0.5 ml |
| 4 | α-tocopherol acetate | 0.05% w/v |
| 5 | Disodium hydrogen phosphate anhydrous | 0.05% w/v |
| 6 | Citric acid monohydrate, | 0.05% w/v |
| 7 | Sodium hydroxide | q.s. to adjust pH |
| 8 | water for injection | q.s. to makeup the volume |

The invention claimed is:

1. A method of treating, preventing or ameliorating a tumor or a symptom arising due to a neurofibromatosis type-2 gene mutation in a subject comprising administering to said subject a therapeutically effective amount of bortezomib.

2. The method as claimed in claim 1, wherein said tumor is a neurofibromatosis type-2/merlin deficient tumor.

3. The method as claimed in claim 2, wherein the neurofibromatosis type-2 deficient tumor is selected from the group consisting of vestibular schwannomas, unilateral schwannomas, bilateral vestibular schwannomas, spinal cord schwannomas, sporadic schwannomas, peripheral nerve schwannomas, meningioma, mesothelioma, ependymoma, glioma, astrocytoma, and combinations thereof.

4. The method as claimed in claim 1, further comprising administering a second ubiquitin-proteasome system inhibitor selected from the group consisting of PI-083, MLN 9708, MLN 4924, MLN 519, Carfilzomib, ONX 0912, CEP-1877, NPI-0052, BU-32 (NSC D750499-S), PR-171, IPSI-001, and a natural product with proteasome-inhibitory effects.

5. The method as claimed in claim 4, wherein the proteasome inhibitor is carfilzomib.

6. The method as claimed in claim 1, wherein the bortezomib is a pharmaceutically acceptable salt, derivative, polymorph, racemate, stereoisomer, conjugate or complex thereof.

7. The method as claimed in claim 1, wherein the bortezomib is administered at a dose in a range of about 0.5 mg/m$^2$ to about 100 mg/m$^2$.

8. The method as claimed in claim 1, wherein the bortezomib is administered in a dose range of about 0.1 mg to about 50 mg per day.

9. The method as claimed in claim 1, wherein the bortezomib is administered via a delivery route selected from the group consisting of parenteral, intra-tumoral, oral, intravenous, transdermal, subcutaneous and intramuscular.

10. The method as claimed in claim 1, wherein the method further comprises administering to said subject one or more additional tumor treatments.

11. The method as claimed in claim 10, wherein the one or more additional treatments are selected from the group consisting of chemotherapeutic agents, radiotherapeutic agents, antibody-based therapeutic agents, steroids, and combinations thereof.

12. A method of enhancing LATS activity in a tumor having compromised activity of neurofibromatosis type-2/merlin comprising administering bortezomib to a subject having the tumor.

13. The method as claimed in claim 12, wherein the tumor is from a schwannoma selected from the group consisting of: a vestibular schwannoma, a unilateral schwannoma, a bilateral vestibular schwannoma, a spinal cord schwannoma, a sporadic schwannoma, and a peripheral nerve schwannoma.

14. The method as claimed in claim 12, wherein the bortezomib is administered in an amount sufficient to increase LATS activity by at least 20%, at least 30%, at least 50%, at least 60%, at least 80%, at least 100%, or at least 150% compared to the activity in an untreated cell having compromised activity of neurofibromatosis type-2/merlin.

15. The method of claim 4, wherein the second ubiquitin-proteasome system inhibitor is a natural product with proteasome-inhibitory effects and said natural product is selected from the group consisting of green tea polyphenol (−)-epigallocatechin-3-gallate (EGCG), curcumin, and soy isoflavone genistein.

16. The method of claim 7, wherein the bortezomib is administered to patients in a dose range of about 0.5 mg/m$^2$ to about 1.3 mg/m$^2$.

17. The method of claim 8, wherein the bortezomib is administered to patients in a dose range of about 1 mg to about 10 mg per day.

18. The method of claim 9, wherein the administration is subcutaneous or intratumoral.

19. The method of claim 18, wherein the administration is subcutaneous.

20. The method of claim 10 wherein the additional treatment is a conventional chemotherapeutic agent.

21. The method of claim 20, wherein the chemotherapeutic agent is selected from the group consisting of alkylating agents, anti-metabolites, plant alkaloids, plant terpenoids, topoisomerase inhibitors, antineoplastics, and combinations thereof.

22. The method of claim 10 wherein the additional treatment is an antibody-based therapeutic agent.

23. The method of claim 22, wherein the antibody-based therapeutic agent is selected from the group consisting of gemtuzumab, alemtuzumab, rituximab, trastuzumab, nimotuzumab, cetuximab, and bevacizumab.

24. The method of claim 10 wherein the additional treatment is a steroid.

25. The method of claim 24, wherein the steroid is dexamethasone.

* * * * *